United States Patent
Krämer

(10) Patent No.: US 7,343,815 B2
(45) Date of Patent: Mar. 18, 2008

(54) QUALITY CONTROL DEVICE FOR SOLID, PHARMACEUTICAL PRODUCTS

(76) Inventor: Thilo Krämer, Röntgenstrasse 68, D-64291 Darmstadt (DE)

( * ) Notice: Subject to any disclaimer, the term of this patent is extended or adjusted under 35 U.S.C. 154(b) by 0 days.

(21) Appl. No.: 10/545,821

(22) PCT Filed: Feb. 12, 2004

(86) PCT No.: PCT/DE2004/000253

§ 371 (c)(1), (2), (4) Date: Sep. 8, 2005

(87) PCT Pub. No.: WO2004/071659

PCT Pub. Date: Aug. 26, 2004

(65) Prior Publication Data

US 2006/0135055 A1    Jun. 22, 2006

(30) Foreign Application Priority Data

Feb. 12, 2003  (DE) ................. 103 05 966
Apr. 7, 2003   (DE) ................. 103 16 024

(51) Int. Cl.
*G01N 3/08*   (2006.01)
*G01N 33/00*  (2006.01)

(52) U.S. Cl. ......................... 73/821; 73/866
(58) Field of Classification Search ............ 73/866, 73/78, 432.1, 821
See application file for complete search history.

(56) References Cited

U.S. PATENT DOCUMENTS 3,757,566 A * 9/1973 Flury ..................... 73/821
4,489,645 A * 12/1984 Sirch et al. ............. 454/187
5,004,576 A *  4/1991 Hinzpeter et al. ....... 264/40.5
6,106,262 A *  8/2000 Levin et al. ............. 425/140
2003/0209098 A1* 11/2003 Kalbermatten ........... 73/866

FOREIGN PATENT DOCUMENTS

DE      3235927        3/1982
JP      11344301 A  * 12/1999

* cited by examiner

*Primary Examiner*—Daniel S. Larkin
*Assistant Examiner*—John Fitzgerald
(74) *Attorney, Agent, or Firm*—Horst M. Kasper

(57) ABSTRACT

The invention relates to a device (17) for the quality control of solid pharmaceutical products such as tablets, comprising a testing means (9) having a sensor for checking one or more parameters of the products. The device (17) consists of a housing (2) and a test chamber (15) that is arranged above said housing (2) and that is formed by a floor (4) and by a protective hood (1) that is placed onto this floor, whereby testing means (9) are located in said chamber. Drives (14) and, if applicable, supply means for the testing means and the transporting means (5, 6, 7) that are arranged in the test chamber (15) are located in the separate housing (2) encapsulated so as to be at least splash-proof and dust-tight vis-à-vis the test chamber (15) and the environment. At least parts of the feed lines (11) leading to the drives and the supply lines that provide energy to the testing means inside the housing (2) pass to the outside of the sealed test chamber (15) in an encapsulated manner so as to likewise be splash-proof and dust-tight.

25 Claims, 6 Drawing Sheets

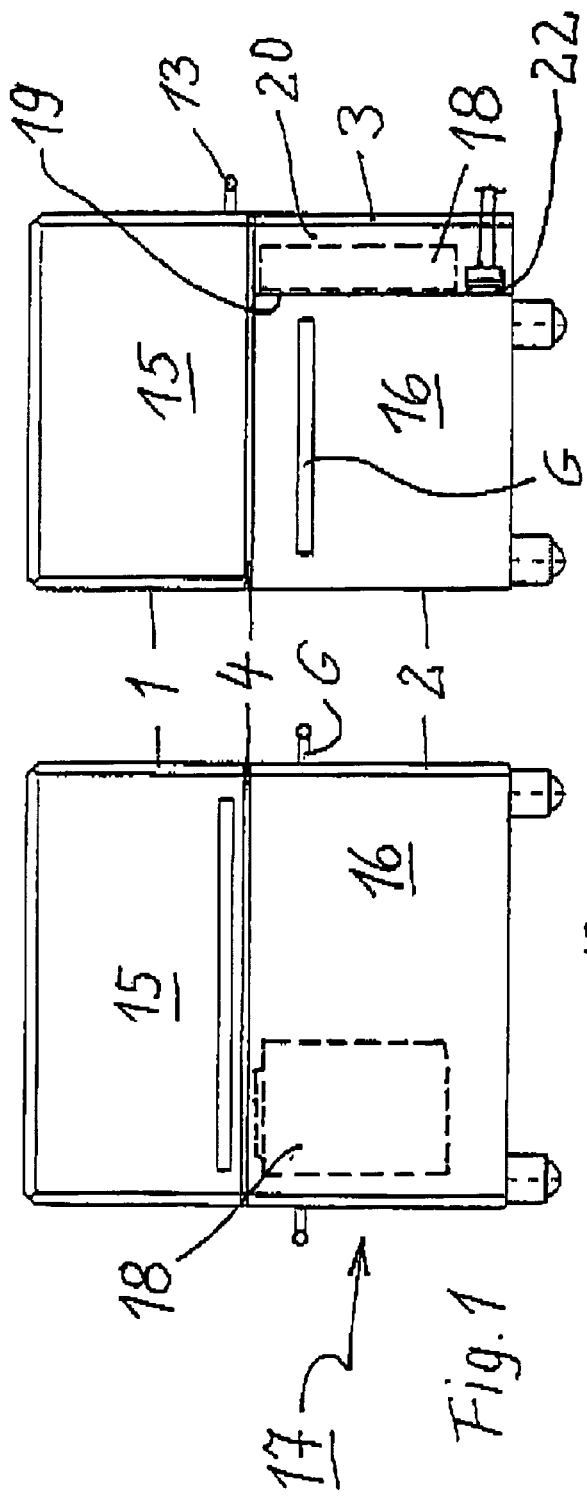

QUALITY CONTROL DEVICE FOR SOLID, PHARMACEUTICAL PRODUCTS

TECHNICAL FIELD

Figure 4:
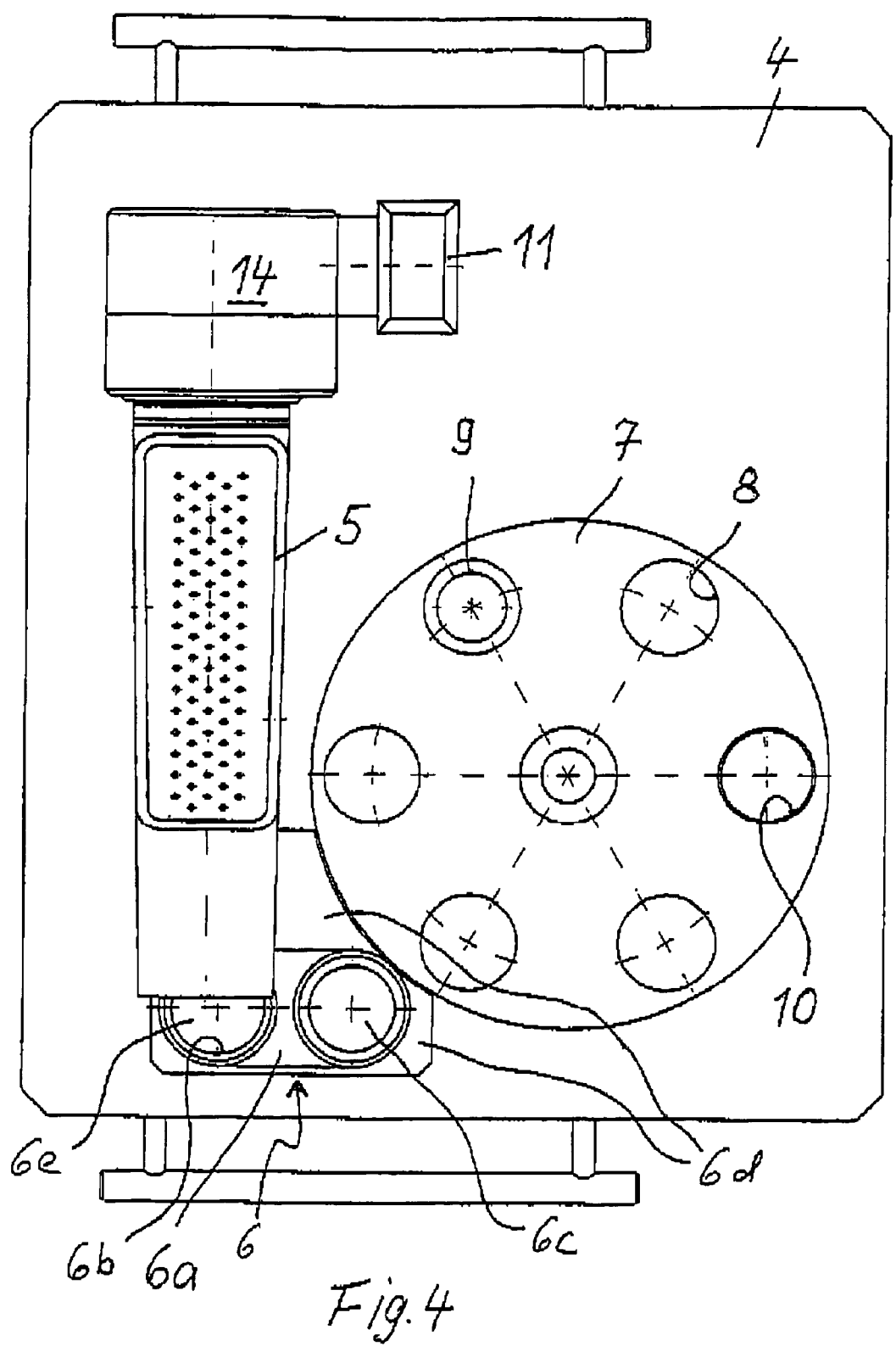

The invention relates to a device for the quality control of solid pharmaceutical products such as tablets, pills, oblongs and the like, comprising at least one testing means and at least one transporting means as well as at least one sensor—such as scales and/or height measuring means and/or force measuring means for measuring the weight and/or the thickness and/or the rupture strength of the product—for checking and ascertaining one or more parameters of the individual pharmaceutical product, said device being of the type described in the main claim.

STATE OF THE ART

Devices for the quality control of solid pharmaceutical products such as, for example, tablets, pills, oblongs and the like are known in which products are fed individually to various testing means that check, for example, the weight, hardness, dimensions, abrasion properties and the like. In a known device of the generic type for quality control, which has a test chamber formed by a protective hood that can be lifted off, homogeneous, solid pharmaceutical products are poured into a storage container, from where they go to a singling trough at whose end the products are individually picked up by a loading means and are each placed by the loading means into a receiving cell of a star feeder that is open towards the test chamber floor. This star feeder can rotate around its vertical axis and is arranged at a small distance parallel to and above the test chamber floor, so that the product lying in the receiving cell cannot end up in the gap between the star feeder and the test chamber floor. While in the receiving cell of the star feeder, the product is conveyed to the weighing platform of scales that are arranged flush in the test chamber floor, for example, in order to determine the weight of the product, and the product is subsequently removed from the receiving cell through a discharge opening located in the test chamber floor, said cell being arranged radially at a distance from the mid-point of the star feeder, so that the rotation of the star feeder causes the receiving cell to move from the scales to above the discharge opening and then the product contained in the receiving cell falls through the discharge opening into a channel that ends above a collecting container, where the tested products can be collected, for instance, for the next testing or checking procedures.

Typically, such a device is employed for the quality control of solid pharmaceutical products for checking procedures that are carried out consecutively on various pharmaceutical products. For this purpose, products are regularly removed from the ongoing production and collected until a sufficiently large number is available for a quality control run.

In order to prevent subsequent quality tests such as, for instance, an analysis of the active ingredients, from being falsified due to dust or other residues from products that were previously tested in the same device, it should be possible to clean the testing means very thoroughly prior to every test run. This is particularly important for combination devices where, in addition to weighing, for example, also hardness testing, thicknesses measurements and the like are conducted, whenever the same device is used for the quality control of other products following hardness tests during which the products are destroyed.

Cleaning such devices is time-consuming since sensitive components such as, for instance, the scales, the controls for the singling trough, the controls for the loading means, the storage means and the like, which are employed to detect and record measured data as well as the appertaining sensors, are situated in the test chamber that is to be cleaned or else the components have openings facing in the direction of the test chamber, so that the operating personnel must be very careful to avoid damage to components, particularly damage caused by cleaning solutions, cleaning materials such as cloths, and the like.

Known devices for quality control of the generic type also entail the draw-back that the feeding, singling, testing and collecting of the products as well as the recording of the acquired test data all take place in one device at its set-up location.

German patent application DE 100 24 598 A1 discloses a device for the automatic quality control of test specimens such as tabs, tablets, pills or dragées for purposes of determining their mechanical-physical properties such as the weight, dimensions, disintegration time in a medium as well as hardness. The device consists of a feed means and a star feeder with peripherally arranged receiving chambers for one test specimen each and a hardness tester, if applicable, a set of scales as well as a means to determine the dimensions of the test specimen, whereby a linear conveyor is connected to one outlet of the star feeder for purposes of taking over the test specimen, said linear conveyor being followed by the hardness tester and being arranged so as to be tangential to the star feeder. The device has a data processing unit that acquires and processes all data by means of a main processor and an auxiliary processor that cooperates with the main processor in order to coordinate the movement of the hardness tester with the running star feeder.

Technical Objective of the Invention

Therefore, the invention is based on the objective of creating a device that serves for the quality control of solid pharmaceutical products, that can be cleaned quickly and particularly thoroughly so as to shorten the change-over times when a switch is made to other products and that allows an evaluation of the obtained test data at any other desired place, in other words, irrespective of where it is located. Thus, it is the aim of the invention to provide a device that can be cleaned thoroughly and quickly as well as automatically and that also makes it possible to forward data remotely.

Disclosure of the Invention and its Advantages

This objective is achieved according to the invention by means of a device for the quality control of solid pharmaceutical products such as tablets, pills, oblongs and the like, comprising at least one testing means that has at least one sensor—such as scales and/or height measuring means and/or force measuring means for measuring the weight and/or the thickness and/or the rupture strength of the product—for checking and ascertaining one or more parameters of the individual pharmaceutical product, and also having a transport means for the products, characterized in that the device has a housing and a test chamber that is arranged above said housing and that can be sealed so as to be splash-proof or water-tight and dust-tight vis-à-vis the environment, said chamber being formed by a floor and by a protective hood that can be placed onto and lifted off this floor, whereby the testing means as well as the transporting means are located in said chamber.

lifted off this floor, whereby the testing means as well as the transporting means are located in said chamber.

According to a variant of the invention, the protective hood can be connected in a detachable manner to the test chamber floor so as to be splash-proof or water-tight and dust-tight.

According to another variant of the invention, the protective hood can be pressed onto the periphery of the test chamber floor and locked in place so as to be splash-proof or water-tight and dust-tight, whereby the protective hood has an encircling gasket that is splash-proof or water-tight and dust-tight on its surface facing the test chamber floor.

The device according to one of Claims 1 to 3, characterized in that the housing can likewise be sealed so as to be splash-proof or water-tight and dust-tight.

According to another variant of the invention, means for driving, controlling and supplying one or more testing means and one or more transporting means are arranged in the housing.

According to another variant of the invention, all of the lines and/or drive shafts leading into or out of the test chamber are configured so as to be splash-proof or water-tight and dust-tight as they pass through the protective hood or the floor.

According to another variant of the invention, the floor has at least one passage, especially for passing lines or a drive shaft through, said passage being sealed by means of a gasket that is splash-proof or water-tight and dust-tight.

According to another variant of the invention, the gaskets are inflatable O-ring gaskets.

According to another variant of the invention, all inlet or feed openings leading into the test chamber as well as all outlet or discharge openings leading out of the test chamber can be hermetically sealed so as to ensure that the test chamber is splash-proof or water-tight.

According to another variant of the invention, the test chamber floor is, at the same time, the wall of the housing.

According to another variant of the invention, means for driving, controlling and supplying the testing means and the transporting means, such as drive aggregates, electric motors, electric controls, signal amplifiers as well as electric and/or optical and/or mechanical connections to supply energy to the testing means are all arranged inside the housing.

According to another variant of the invention, an interface that is accessible from outside of the housing is arranged on the housing, preferably on its front wall, whereby a plurality of electric lines leading into or out of the housing open into said interface and the latter serves to establish an electric connection for the device and/or to transmit electric signals and/or data between the device and the outside world.

According to another variant of the invention, a hinged door is arranged on the housing in such a way as to form an antechamber between the housing and the hinged door.

According to another variant of the invention, the device encompasses the following additional components:
- a singling means as part of the transporting means arranged inside the test chamber, whereby the pharmaceutical products can be fed from the storage container to the singling means;
- a conveying means as another part of the transporting means that is arranged above the test chamber floor and that has at least one receiving cell open towards the floor into which one product from the singling means can be introduced, whereby the product accommodated in the receiving cell can be fed to the testing means;
- a discharge opening to which the product—after it has been tested by the testing means—can be fed during the further course of transportation by the conveying means, whereby the product reaches the discharge opening and then falls through it, as a result of which it is removed from the receiving cell;
- as well as a collecting container situated below the discharge opening that serves to receive the tested products or parts thereof once they have fallen through the discharge opening.

According to another variant of the invention, the transporting means is a star feeder that is arranged parallel to the floor and that can rotate around a vertical axis, whereby the receiving cell is situated in the vicinity of the outer circumference of the star feeder and whereby the testing means as well as the discharge opening are arranged in such a way that, as the star feeder turns in its direction of rotation, each product accommodated inside the receiving cell first reaches the testing means and subsequently the discharge opening.

According to another variant of the invention, the discharge opening is a hole in the test chamber floor, whereby the collecting container is located in the antechamber.

According to another variant of the invention, the test chamber floor has a rim around the discharge opening.

According to another variant of the invention, the testing means is a set of scales equipped with a weighing platform and a load cell.

According to another variant of the invention, the inside of the housing can be charged with positive pressure relative to the environment and/or to the test chamber.

According to another variant of the invention, the test chamber can be charged with negative pressure relative to the environment.

According to another variant of the invention, the housing is situated next to the test chamber floor rather than below it.

According to another variant of the invention, the device has rollers or wheels on which the device can be moved.

According to another variant of the invention, the front wall of the housing consists of a frame and of a removable front plate that can be placed onto the frame so as to be water-tight.

According to a variant, the device according to the invention for the quality control of solid pharmaceutical products such as tablets, pills, oblongs and the like comprises at least one testing means that has at least one sensor—such as scales and/or height measuring means and/or force measuring means for measuring the weight and/or the thickness and/or the rupture strength of the product—for checking and ascertaining one or more parameters of the individual pharmaceutical product, whereby the device consists of a housing with a test chamber that is arranged above said housing and that is formed by a floor and by a moveable protective hood that can be placed onto this floor, whereby the testing means as well as the transporting means are located in said chamber, whereby the drives and, if applicable, supply means for the testing means and the transporting means that are arranged in the test chamber are, in turn, located in the separate housing encapsulated so as to be at least splash-proof and dust-tight vis-à-vis the test chamber and the environment and whereby at least parts of the feed lines leading to the drives and the supply lines that provide energy to the testing means inside the housing pass to the outside of the test chamber in an encapsulated manner so as to likewise be at least splash-proof and dust-tight.

According to another variant of the invention, the feed lines leading to the drives and, if applicable, to the supply means that provide energy to the testing means and to the transporting means pass through the test chamber floor into a receiving chamber located below the sealed test chamber and formed by the housing, so that the device is divided by the test chamber floor into the test chamber and into the receiving chamber of the housing, whereby the housing that encloses the receiving chamber can likewise be closed by a door or the like so as to be water-tight and dust-tight, and the means for driving, controlling and supplying the testing means and the transporting means, such as drive aggregates, electric motors, electric controls, signal amplifiers as well as electric and/or optical and/or mechanical connections to supply energy to the testing means are all arranged inside the receiving chamber.

According to another variant of the invention, the housing of the receiving chamber has at least one interface that is accessible from outside of the housing, preferably in the front wall of the housing, and that serves to establish a connection for electric and/or optical and/or mechanical connections for supplying energy to the testing means and for connecting a computer or the like for function monitoring as well as for detecting and forwarding test data from the sensors, so that the device can be controlled and the test data can be evaluated irrespective of the set-up location of the device.

According to another variant of the invention, the protective hood can likewise be pressed onto the periphery of the test chamber floor and locked in place so as to be water-tight and dust-tight.

According to another variant of the invention, the protective hood has an encircling gasket on its surface facing the test chamber floor.

According to another variant of the invention, the test chamber floor as well as the protective hood extend beyond the housing of the receiving chamber on at least one side, preferably the front of the housing, whereby a hinged door is arranged on the housing and it separates off another chamber below the floor and between the front of the housing located across from the hinged door, namely, the antechamber into which the interface opens that is accessible from the outside.

According to another variant of the invention, the device has a singling means arranged inside the test chamber, to which singling means the pharmaceutical products can be fed from a storage container, whereby the device has a transporting means that is arranged above the test chamber floor and that has at least one receiving cell open towards the floor into which one product from the singling means can be introduced, whereby the product in the receiving cell is fed to at least one testing means that is preferably located below the transporting means and that checks the product in terms of its weight and/or dimensions and/or hardness and/or abrasion properties, and the product—after it has come from the testing means—is removed from the receiving cell via a discharge opening located in the floor into which the product falls over the further course of transportation after being tested, whereby a collecting container is situated below the discharge opening that serves to receive the tested products or parts thereof.

According to another variant of the invention, the transporting means is a star feeder that can rotate around its vertical axis and that has at least one receiving cell on its outer circumference and, in its direction of rotation, the testing means comes first, followed by the discharge opening in the direction of rotation.

According to another variant of the invention, the discharge opening is located in the part of the test chamber floor that extends beyond the housing of the receiving chamber, whereby the collecting container situated below the discharge opening is located in the additional free space that is separated off by the hinged door.

According to another variant of the invention, the testing means is a set of scales equipped with a weighing platform and a load cell, whereby the weighing platform is arranged above the test chamber floor and the floor under the weighing platform has a rim, and the weighing platform has a recess to receive a rim, so that the interaction of the rim and the recess on the weighing platform creates a labyrinth gasket that is at least splash-proof.

According to another variant of the invention, the star feeder is arranged at a distance parallel to the test chamber floor, by the height of the weighing platform above the floor, whereby at least one plate can be placed onto the floor whose thickness matches the height of the weighing platform above the test chamber floor, and whereby the plate has recesses for the discharge opening, the weighing platform, the passage for the drive shafts of the star feeder and the like.

According to another variant of the invention, the load cell of the scales can be arranged directly below the weighing platform.

According to another variant of the invention, the test chamber floor has a rim around the discharge opening.

According to another variant of the invention, the discharge opening can be sealed by a plug.

According to another variant of the invention, electric and/or optical connections for connecting a computer or the like for function monitoring and for detecting and forwarding the test data are arranged in or on the wall of the housing inside the additional chamber separated by the hinged door, that is to say, the antechamber, whereby the computer can be arranged in this chamber.

According to another variant of the invention, the protective hood can only be opened or locked after the hinged door on the test chamber floor has been opened.

According to another variant of the invention, the interior of the housing that forms the receiving chamber can be charged with a constant positive pressure relative to the environment and/or the test chamber.

According to another variant of the invention, the test chamber can be charged with a constant negative pressure relative to the environment.

According to another variant of the invention, the device consists of a housing with a closeable test chamber that is arranged above said housing and that is formed by a floor and by a moveable protective hood that can be placed onto this floor, whereby the testing means as well as the transporting means are located in said chamber, whereby the drives and, if applicable, supply means for the testing means and the transporting means that are arranged in the test chamber are, in turn, located in the separate housing encapsulated so as to be water-tight and dust-tight vis-à-vis the test chamber and, if applicable, also vis-à-vis the environment.

In an advantageous embodiment of the invention, at least parts of the feed lines leading to the drives and to the supply means that provide energy to the testing means as well as to the transporting means inside the housing pass to the outside of the test chamber in a manner so as to be water-tight and dust-tight. In another embodiment of the invention, all of the passages through the floor that serve to pass the feed lines through and that serve to accommodate the testing means are equipped with water-tight gaskets which can be, for instance, inflatable O-ring gaskets.

In comparison to the state of the art, the device according to the invention for the quality control of solid, pharmaceutical products entails the advantage that the drives and supply lines as well as the signal amplifiers for all of the devices for singling, transporting and testing the products arranged in a test chamber that can be closed by a protective hood are accommodated in housings that are splash-proof or water-tight and dust-tight vis-à-vis the test chamber, so that, for instance, cleaning work involving cleaning solutions, power washers and the like can be carried out quickly and simply, whereby the lines that supply energy to the drives, supply means and signal amplifiers from the sealed housings to the outside of the test chamber are configured so as to be splash-proof or water-tight.

In an advantageous embodiment of the invention, the feed lines leading to the drives and, if applicable, to the supply means that provide energy to the testing means and to the transporting means pass through the test chamber floor into the receiving chamber that is located below the sealed test chamber and that is formed by the housing, so that the device is divided by the test chamber floor into the test chamber, on the one hand, and into the receiving chamber of the housing, on the other hand, whereby the housing that encloses the receiving chamber can be closed by a door or the like so as to be water-tight and dust-tight, and means for driving, controlling and supplying the testing means and the transporting means, such as drive aggregates, electric motors, electric controls, signal amplifiers as well as electric and/or optical and/or mechanical connections for supplying energy to the testing means are all arranged inside the receiving chamber. In this manner, the device can be cleaned completely, thoroughly and especially automatically. In order to do so, after the device has been used for its intended purpose, all inlet or feed openings as well as all outlet or discharge openings are hermetically sealed so as to be water-tight, and so are all of the passages through the floor of the sealed test chamber, for instance, by O-rings which, in a special embodiment, can also be inflatable. Thus, the test chamber can be made as water-tight as an aquarium. Then water is filled into the test chamber and the drives of the device are turned on, so that all of the rotating parts or parts that move back and forth inside the sealed test chamber move within the water bath, as a result of which they perform an automatic cleaning procedure. Subsequently, if necessary, the device can be brought to a clean room.

In another advantageous embodiment of the invention, the housing of the receiving chamber, preferably in the front outer wall of the housing, has at least one interface that is accessible from outside of the housing and that serves to establish a connection for electric and/or optical and/or mechanical connections for supplying energy to the testing means and for connecting a computer or the like for function monitoring and for detecting and forwarding test data from the sensors, so that the device can be controlled and its function can be monitored and the test data can be evaluated irrespective of the set-up location of the device and of any cleaning work that might be necessary. The interface eliminates the need for passages for cables and the like through the housing wall, thus ensuring that the device can be configured so as to be water-tight and dust-tight. Therefore, the test chamber floor as well as the protective hood extend beyond the housing of the receiving chamber on at least one side, preferably on the front of the housing, whereby a hinged door is arranged on the housing and it separates another chamber below the test chamber floor and between the front of the housing located across from the hinged door, into which chamber the interface opens that is accessible from the outside.

In an advantageous embodiment of the invention, the protective hood seals the test chamber vis-à-vis the environment so as to be water-tight and dust-tight in order to prevent abrasion dust or the like from being discharged out of the test chamber, and the protective hood can be locked and pressed onto the test chamber floor.

In another embodiment of the invention, the protective hood has an encircling gasket on its surface facing the test chamber floor, so that a tight seal can be attained when the protective hood is pressed down, as a result of which dirt or residues of tested products on the contact surface between the test chamber floor and the protective hood cannot have a detrimental impact on the sealing of the test chamber vis-à-vis the environment.

In another advantageous embodiment of the invention, the receiving chamber only occupies part of the surface area below the test chamber floor, so as to create an additional chamber that is separated from the environment by a door or the like and that is water-tight and dust-tight vis-à-vis the receiving chamber into which the externally accessible interface of the receiving chamber opens up. The tested products can be captured through a discharge opening in the test chamber floor in a collecting container arranged below the test chamber floor.

In an advantageous embodiment of the invention, the transporting means is a driven star feeder that rotates around its vertical central axis and that, on its outer circumference, has at least one receiving cell that is open towards the test chamber floor to accommodate a product to be tested, whereby the rotation of the star feeder causes the products contained in the cells to be conveyed to various testing means, and the tests are carried out on the product in the receiving cell lying on the test chamber floor, so that, as the star feeder rotates further, the product can be conveyed to another testing means and ultimately reaches the discharge opening and falls through it.

In another advantageous embodiment of the invention, the discharge opening opens up into the chamber that is separated from the receiving chamber and from the environment so as to be water-tight and dust-tight, whereby said chamber can be locked by a hinged door or the like, and the externally accessible interface of the receiving chamber can also be reached from there.

An especially advantageous embodiment of the invention provides that, particularly in order to render the arrangement of the scales in the test chamber water-tight, the weighing platform is placed at an elevated position above the test chamber floor. Below the weighing platform, the test chamber floor has a rim that, together with the weighing platform fitted with a recess to receive the rim, forms a labyrinth gasket that is liquid-tight and dust-tight, so that no cleaning solution can penetrate the housing located underneath. At the same time, the rim can serve to limit the path of the weighing platform, so that the sensitive scales cannot be overloaded during the cleaning procedure. Moreover, this arrangement makes it possible to remove the weighing platform in order to perform maintenance work and the like, for instance, to clean the guide of the stamp used to press the weighing platform onto the load cell. The drive shaft of the star feeder can likewise be sealed by means of a rim although, in an advantageous manner, instead of or in addition to the rim, an axially sealing bearing is employed so that the drive shaft can pass through the test chamber.

In another particularly advantageous embodiment of the invention, in order to allow the feed of the test objects via a star feeder onto the weighing platform located above the test chamber, at least a single-part or multi-part plate is laid onto the test chamber floor between the latter and the star feeder, said plate having openings for the drive shaft of the star feeder, the weighing platform, the discharge opening for the test objects and, if applicable, for other test means and for the drive of the loading means, whereby the thickness of said plate matches the installation height of the weighing platform above the test chamber floor. Both the star feeder and the plate located below it can be lifted off so as to facilitate, for example, cleaning work once these components have been removed.

In an advantageous embodiment of the invention, the load cell of the scales is arranged directly below the weighing platform so that it becomes possible to dispense with sealing the passage for the stamp of the weighing platform that presses onto the load cell, so that only the electric, and optionally, optical connections of the load cell with the signal amplifiers inside the housing have to pass through the housing wall.

In an advantageous embodiment of the invention, the discharge opening is fitted with a rim that prevents cleaning solution from flowing out through the discharge opening, whereby the height of the rim above the test chamber floor is less than the distance between the bottom of the star feeder and the test chamber floor.

In another advantageous embodiment of the invention, the discharge opening is designed so that it is closed or can be closed by a plug during cleaning work and the like.

In another embodiment of the invention, in addition to the collecting container, there is a computer or the like for recording and processing the measured values arranged in the chamber that is separated from the receiving chamber, that is accessible through the hinged door and that is located below the test chamber floor, whereby, via electric and/or optical connections arranged in the separation wall leading to the receiving chamber, the computer can be connected to the signal processing means and to the signal amplifier of the scales, to the controls for the drives of the singling trough, the loading means and the star feeder as well as, optionally, to additional measuring and testing means that are connected to the weighing device.

In an additional advantageous embodiment of the invention, the protective hood can be closed by a lock that can only be operated from the chamber located below the test chamber floor and accessible through the hinged door.

In an additional advantageous embodiment, a constant negative pressure is generated in the receiving chamber below the test chamber, so that a constant stream of air exits through any gaps that might be present at the passages for the drive shafts and the like in the housing, particularly during the cleaning procedure.

In another advantageous embodiment of the invention, a constant negative pressure is maintained in the test chamber so as to prevent abrasion dust or the like from escaping from the test chamber during the testing of, for instance, hormone products or antibiotics.

In another advantageous embodiment of the device, the housing, which is hermetically sealed vis-à-vis the test chamber, along with the receiving chamber that is enclosed by the housing, is arranged next to the test chamber floor instead of below it.

According to another variant of the invention, the device consists of a housing and of a closeable test chamber arranged above said housing, the chamber being formed by a floor and by a movable protective hood that can be placed onto this floor, where both the testing means and the transporting means are located, whereby the drives and, if applicable, supply means for the testing means and the transporting means that are arranged in the test chamber are arranged in the separate housing that is encapsulated so as to be water-tight and dust-tight, if applicable, also vis-à-vis the environment.

According to another variant of the invention, at least parts of the feed lines leading to the drives and the supply means that provide energy to the testing means and to the transporting means inside the housing are encapsulated so as to be water-tight and dust-tight as they pass to the outside of the test chamber.

According to another variant of the invention, the passages through the floor for passing through the feed lines as well as for receiving the testing means are configured with water-tight gaskets.

According to another variant of the invention, the device has a singling means as the transporting means arranged inside the test chamber, to which singling means the pharmaceutical products can be fed from a storage container, whereby the device has another transporting means arranged above the test chamber floor that has at least one receiving cell that is open towards the floor into which one product from the singling means can be introduced, whereby the product in the receiving cell can be fed to at least one testing means preferably located below the transporting means for checking the product in terms of its weight and/or dimensions and/or hardness and/or abrasion properties, and the product, after the checking procedure and during the further course of transportation, can be removed from the receiving cell through a discharge opening into which the product falls and that is located downstream from the testing means, whereby a collecting container is situated below the discharge opening and it serves to receive the tested products or parts thereof.

According to another variant of the invention, the testing means is a set of scales equipped with a weighing platform and a load cell, whereby the weighing platform is arranged above the test chamber floor and the floor has a water-tight gasket under the weighing platform or inside the weighing platform.

According to another variant of the invention, the floor below the weighing platform has a rim, whereby the weighing platform has a recess to receive the rim, so that the interaction of the rim and the recess on the weighing platform creates a water-tight gasket, especially a labyrinth gasket.

According to another variant of the invention, the drives and, if applicable, supply means for the testing means and the transporting means that are arranged in the test chamber are arranged in a separate housing encapsulated so as to be splash-proof and dust-proof at least vis-à-vis the test chamber and the environment, whereby at least parts of the feed lines leading to the drives and the supply means that provide energy to the testing means inside the housing are likewise encapsulated so as to be splash-proof and dust-tight as they pass to the outside of the test chamber.

According to another variant of the invention, the housing, which is hermetically sealed vis-à-vis the test chamber, along with the receiving chamber that is enclosed by the housing, is arranged next to the test chamber floor instead of below it.

BRIEF DESCRIPTION OF THE DRAWINGS, WHERE THE FOLLOWING IS SHOWN

Figure 5:
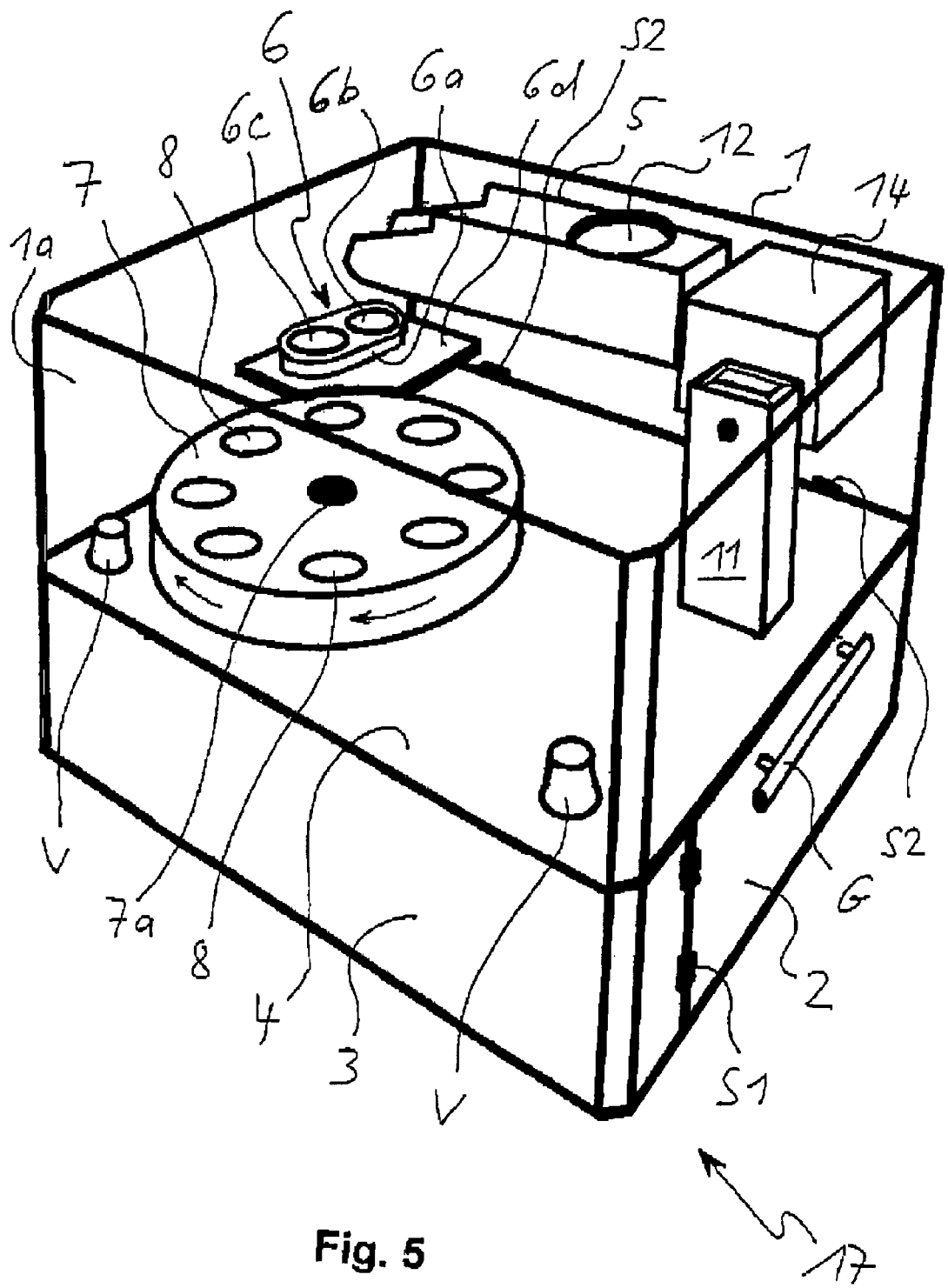
Figure 6:
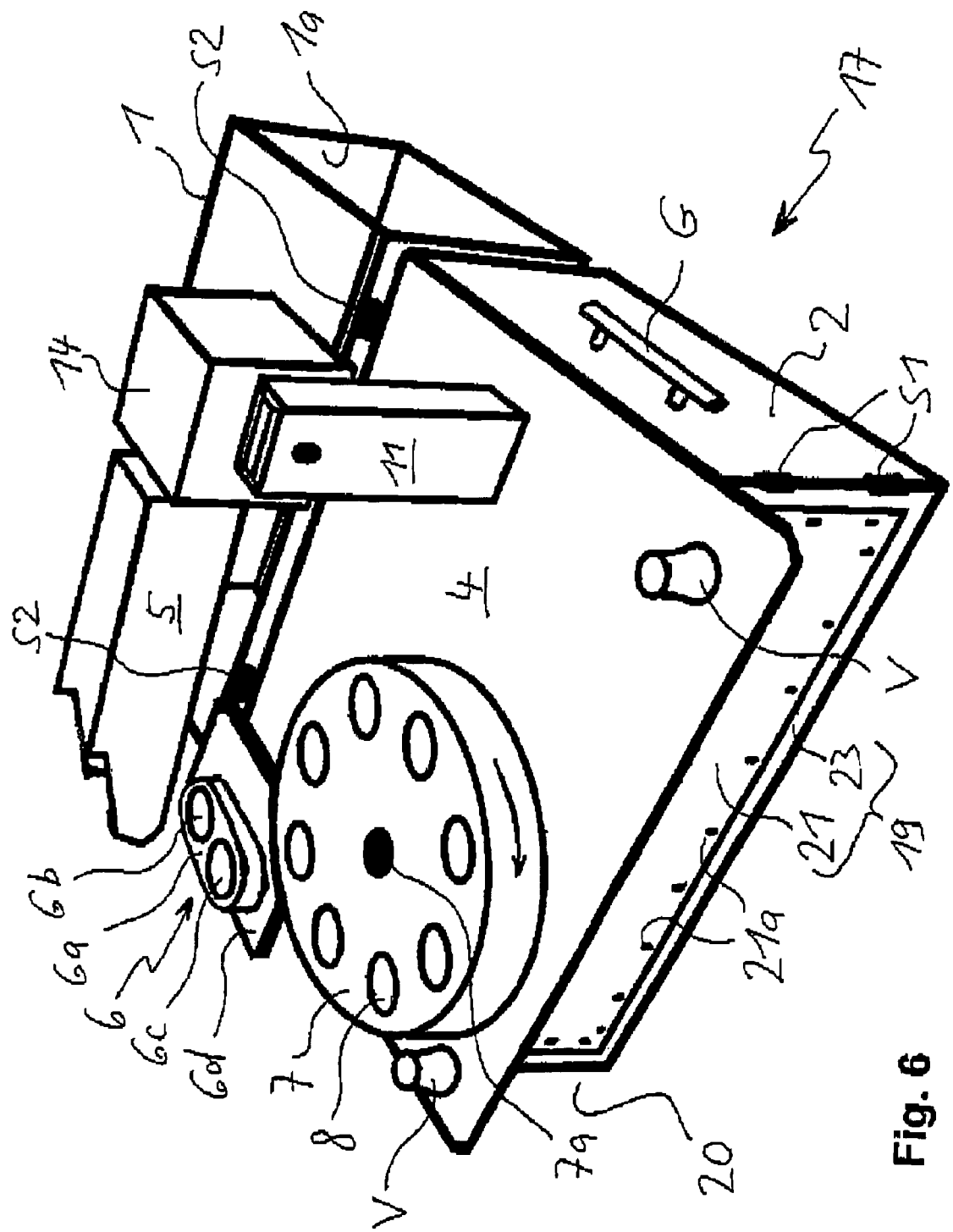
Figure 7:
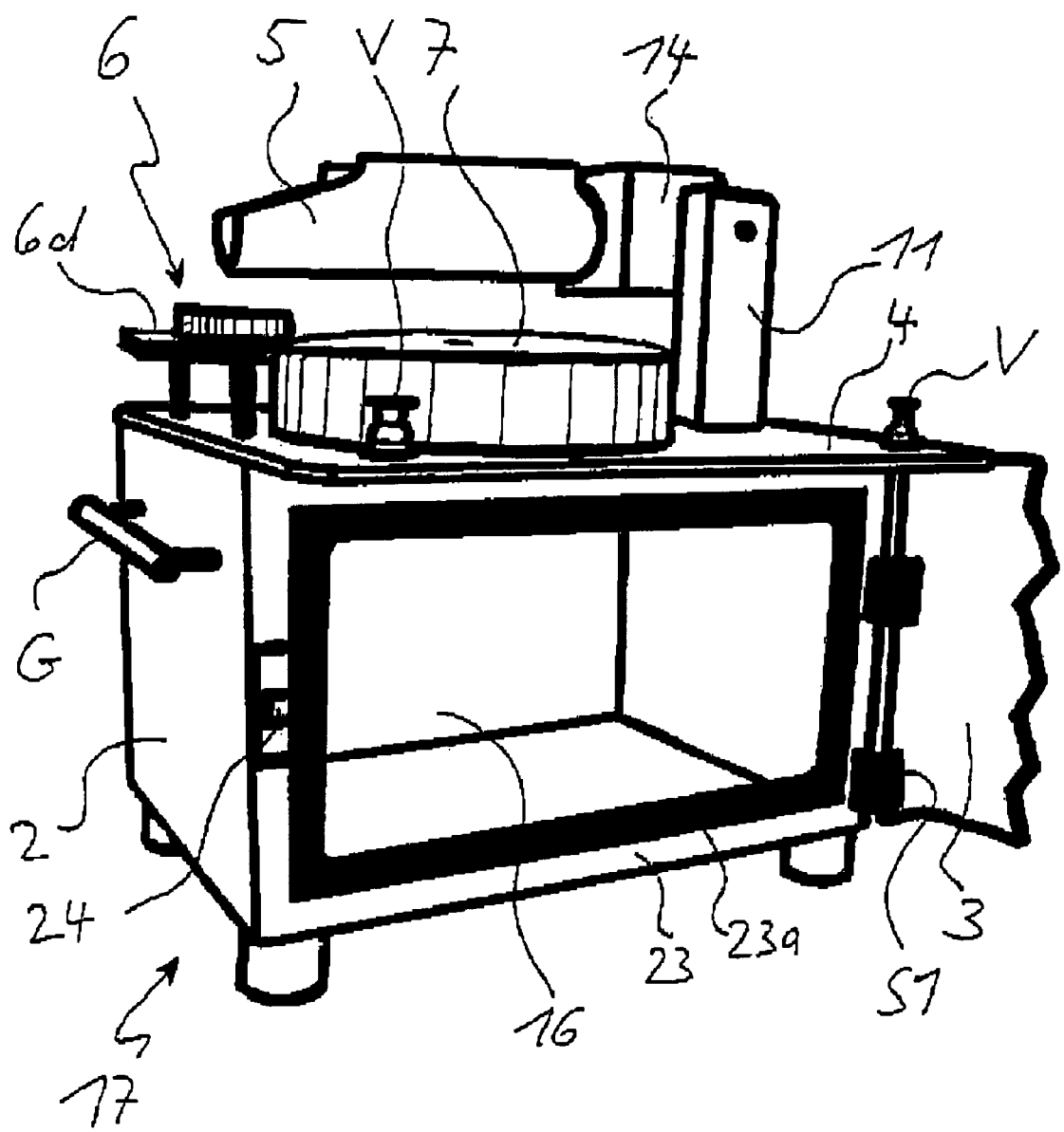
Figure 8:
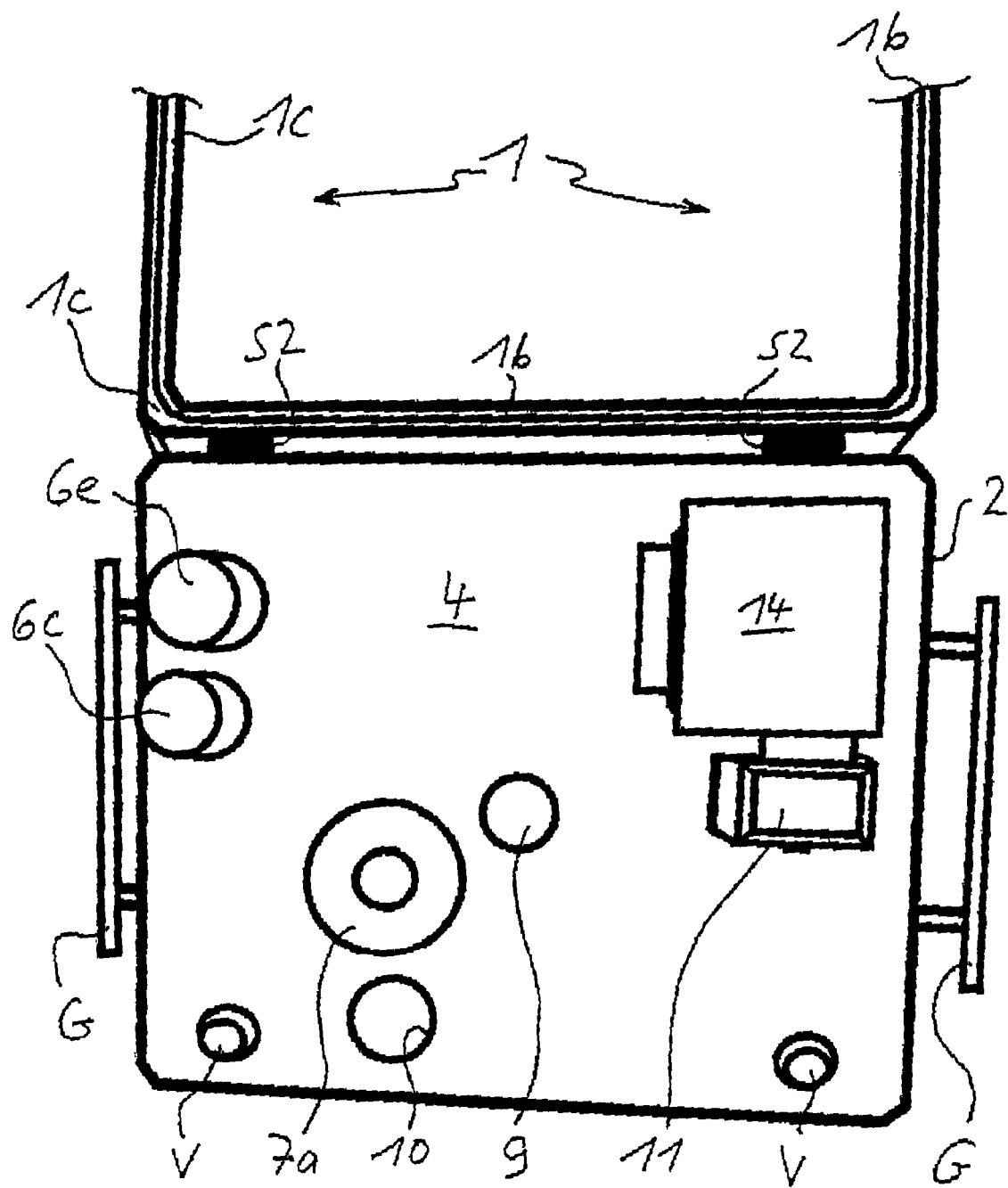

FIG. 1 a front view of a device according to the invention;
FIG. 2 a side view of the device of FIG. 1 rotated clockwise by 90°;

FIG. 3 a top view of the device of FIG. 1;

FIG. 4 a top view of the device of FIG. 1 once the protective hood has been removed;

FIG. 5 a perspective view of the device of FIG. 1 with a singling means, loading means, star feeder and closed protective hood as well as a closed hinged door;

FIG. 6 a perspective view of the device of FIG. 1 with an open protective hood, whereby the hinged door is not shown;

FIG. 7 a perspective front view of the device of FIG. 1 when the front wall has been removed, whereby the protective hood is not shown, while the hinged door is only partially shown; and FIG. 8 a perspective top view of the device of FIG. 1 with an open protective hood, whereby the singling means and the star feeder are not shown, while the loading means is only partially shown.

The figures are merely schematic depictions.

DESCRIPTION OF THE EMBODIMENT

The device 17 for the quality control of solid pharmaceutical products—which is shown in a front view in FIGS. 1, 2 and 3, in a side view rotated clockwise by 90° and in a top view—consists of a cuboid housing 2 and it has a test chamber 15 closed by a transparent hood 1, whereby the front of the hood has a handle 13 for lifting off and swiveling the protective hood 1. Likewise, the upper covering surface of the protective hood 1 has an opening 12 through which the pharmaceutical products enter the test chamber 15.

The test chamber 15 is separated from the housing 2 by a test chamber floor 4 so that a water-tight and dust-tight receiving chamber 16 is created below the test chamber floor 4 of the device 17 inside the housing 2, said receiving chamber 16 serving to accommodate the necessary controls and drives of the means that are present in the test chamber and that are used for singling, transporting and testing pills, tablets or the like. Likewise arranged in the receiving chamber 16 are signal amplifiers for the testing means used to measure, for example, the weight, dimensions and hardness and these are likewise encapsulated so as to be water-tight.

A hinged door 13, which is installed on the front of the housing 2 of the device 17, closes the receiving chamber 16 that is separated water-tight and dust-tight inside the housing 2 and that is below the test chamber floor 4 of the device 17, said receiving chamber 16 being able to accommodate, for example, a computer or the like for purposes of acquiring test data. The front wall 19 of the housing 2 is recessed with respect to the test chamber floor 4, as depicted in FIG. 2, so that a free space 20 separated by the hinged door 3 is formed between the hinged door 3 and the front wall 19 of the housing 2, and a collecting container 18 for the tested products is arranged in said free space 20. In order to cover the collecting container 18 and to form the free space 20, the hinged door 3 is angled at both ends, so that the hinged door 3 has a double-L shape as seen from above.

Inside the front wall 19 of the housing 2, there is also an interface (not shown here) for the connection of all electric, mechanical or pneumatic aggregates. Except for the protective hood 1, the device is preferably made of stainless steel.

FIG. 4 shows a top view of a device according to the invention for the quality control of solid pharmaceutical products when the protective hood 1 has been removed. The products to be tested, for instance, tablets, are fed from a storage container (not shown here)—which can be located inside or outside of the test chamber 15—to a singling means 5 which, in the example shown, is a shaking trough 5 that is driven by an electric motor 14. At the end of the singling means 5, the products fall individually into a loading means 6. This loading means 6 can be rotated around an axis and it feeds the tablets individually to a rotatable star feeder 7 that has several receiving cells 8 distributed peripherally along its circumference. Between the star feeder 7, which can be lifted off in the direction of the observer, and the test chamber floor 4, there is a plate that can likewise be lifted off in the direction of the observer and that has recesses for the drive shaft that imparts the swiveling movement of the loading means 6, for the drive shaft of the star feeder 7, for the scales 9 and for the discharge opening 10. In the area around the loading means 6, the plate is elevated by the thickness of the star feeder 7, so that the loading means 6 is positioned flush above the star feeder 7 and the products can be pushed by the loading means 6 over the edge of the star feeder 7 in such a way that they fall from the top into the receiving cells 8 of the star feeder 7. The receiving cells 8 are holes and are thus open in the direction of the test chamber floor 4.

As a result of the clockwise rotational movement of the star feeder 7 around its central axis perpendicular to the plane of observation, the tablets are fed via a weighing platform 9 that is raised with respect to the test chamber floor 4 by the thickness of the plate positioned between the star feeder 7 and the test chamber floor 4 to a set of scales that are arranged in the housing 2 and that are flush with the plate. Subsequently, the weighed products are conveyed by the rotational movement of the star feeder 7 to a discharge opening 10 through which they fall into the collecting container 18 positioned behind the hinged door 3.

In order to configure the receiving chamber 2 water-tight, for example, the electric motor 14 of the singling means 5 is in a rectangular pipe 11 that has been welded onto the test chamber floor 4 and that is closed in the direction of the observer, so that only the passages for the drive shafts and for the stamp that is arranged below the weighing platform 9 and that presses onto the load cell of the scales pass through the receiving chamber 3 which can otherwise be closed so as to be water-tight and dust-tight.

For the cleaning procedure, according to the method, all of the feed and discharge openings or inlet and outlet openings are hermetically sealed so as to be water-tight, except for one opening through which air can be vented. Then water is filled into the test chamber 15, for example, using a hose connection provided for this purpose, and then the opening for venting air out of the test chamber 15 is likewise closed. Now all of the movable aggregates such as the shaking trough 5, star feeder 7, loading means 6, in certain cases also the drive shaft for the swiveling movement of the loading means 6 are put into motion inside the water bath by their drive aggregates, so that the movement of the aggregates inside the water bath creates a vigorous turbulence, which results in a thorough cleaning. After the water has been drained, an air drying procedure can be carried out with hot air that is simultaneously fed in via the feed opening and blown out via the discharge opening.

FIG. 5 shows a schematic perspective view of the device 17 of FIG. 1 with the singling means 5, the loading means 6, the star feeder 7 and the closed protective hood 1 as well as the closed hinged door 3. The hinged door 3 is joined to the housing 2 by means of hinges S1.

According to the invention, the device 17 serves for the quality control of solid pharmaceutical products such as tablets, pills, oblongs and the like. The housing 2 is arranged below the test chamber 15 that can be closed so as to be splash-proof or water-tight and dust-tight vis-à-vis the environment, said chamber 15 being formed by the floor 4 and by the protective hood 1 that can be placed onto and lifted off this floor.

The floor 4 of the test chamber 15 concurrently forms the upper wall of the housing 2 and of the antechamber 20 located between the hinged door 3 and the housing, as a consequence of which it is not visible in FIG. 5. The handle 13 that serves to open the protective hood 1 is not shown in FIG. 5.

The protective hood 1 is joined to the housing by means of hinges S2 and it is pressed onto the floor 4 by means of locks V so as to be water-tight and dust-tight. For this purpose, the locks V each have an extension that is capable of exerting pressing force in the direction of the floor 4 onto a projection arranged on the inside of the front wall 1a of the protective hood 1. These extensions and projections are not shown in the figures. The locks V can be activated and deactivated by means of control elements (which are likewise not shown), that is to say, the protective hood can be locked and unlocked by means of the control elements. For the sake of easier handling, the housing 2 has side handles G.

In order for the pharmaceutical products to be tested, they are introduced into the singling means 5 via the filling opening. The mode of operation of such a singling means is described in German patent DE 38 64 82.2.

The electric motor 14 is secured on a stand by means of the rectangular pipe 11.

The loading means 6 has an encircling element 6a with an indentation 6b, a loading shaft 6c and a plate-like substrate 6d. The encircling element 6a is affixed to the loading shaft 6c so that it cannot rotate. The singling means 5 is arranged on the electric motor 14 in such a way that the singled products fall out of the singling means 5 individually one at a time into an indentation 6b of the encircling element 6a that is open towards the top and the bottom.

Below the indentation 6b, there is an impact sensor 6e (not depicted in FIG. 5; see FIG. 8) that detects the fall of a product into the indentation 6b and, by means of another electric motor (not shown here), imparts a loading shaft 6c with such a swiveling movement that the indentation 6b moves above a receiving cell 8 of the star feeder 7 that is open towards the top and the bottom. The star feeder 7 can be rotated in increments by means of a rotation shaft 7a. Here, the rotational movement of the star feeder 7 is synchronized with the swiveling movement in such a way that, at the end of every swiveling movement, the indentation 6b is positioned above one of the receiving cells 8. The product is thus transported by the swiveling movement from the impact sensor 6a over the substrate 6d to a receiving cell 8 and falls into it. This procedure is repeated every time when one of the products to be tested falls into the indentation 6b. The tops of the impact sensor 6e, of the substrate 6d and of the star feeder 7 are preferably on the same level.

In the present example, the testing of the pharmaceutical product consists of a weighing procedure. The star feeder 7 rotates once the product has fallen into the receiving cell, in this manner conveying the product to the scales 9, which are not shown in FIG. 5 and, after completion of the weighing procedure, to the discharge opening 10 (not shown in FIG. 5) arranged below the star feeder 7, so that the product falls through the opening and reaches the collecting container 18.

The singling means 5, the loading means 6 and the star feeder 7 together form a transporting means for the products. Naturally, other parameters of the individual pharmaceutical product can be tested or measured such as, for instance, the height and the rupture strength of the product before it is fed to the discharge opening 10.

According to the invention, the test chamber 15 can be closed so as to be splash-proof or water-tight and dust-tight. In particular, this is extremely advantageous if the test chamber 15 is to be cleaned, for instance, by being rinsed, after environmentally toxic or health hazardous pharmaceutical products have been tested with the device 17 since this ensures that no residues or dust from the product can reach the environment in an uncontrolled manner. In the case of a water-tight version, it is advantageously possible to even completely flood the test chamber 15.

FIG. 6 shows a perspective view of the device 17 when the protective hood 1 is completely open, whereby the hinged door 3 of FIG. 5 is not shown. Therefore, the antechamber 20 can be clearly seen in FIG. 6. In the example of FIG. 6, the front wall 19 of the housing 2 consists of an encircling frame 23 and a front plate 21 that is placed onto it and affixed by means of screws 21a. According to a preferred embodiment of the invention, the housing 2 is likewise configured in such a way that it can be closed so as to be splash-proof or water-tight and dust-tight. Therefore, the front plate 21 is preferably placed onto the frame 23 in a manner that is splash-proof or water-tight and dust-tight. In FIG. 6, the protective hood 1 is shown swiveled on the hinge S2 towards the back.

FIG. 7 shows a perspective front view of the device 17 when the front wall 21 has been removed, whereby the protective hood 1 is not shown while the hinged door 3 is only partially shown. An encircling gasket 23a runs along the inside of the frame 23, said gasket serving to seal off the front plate 21 with respect to the frame 23. Likewise arranged on the frame 23 opposite from the hinges S1 is a closing mechanism 24 that serves to lock the hinged door 3 in the closed position.

FIG. 8 shows a perspective top view of the device 15 when the protective hood is open, whereby the singling means 5 and the star feeder 7 are not shown while the protective hood 1 as well as the loading means 6 are each only partially shown. The protective hood 1 is completely open and is located in the position already shown in FIG. 6. The front surface 1c of the protective hood 1 that points downwards when the protective hood 1 is in the closed position and therefore faces the floor 4 has an encircling gasket 1b that is capable of sealing off the front surface 1c so that it is splash-proof or water-tight and dust-tight with respect to the floor 4.

The star feeder 7 is not shown in FIG. 8, as a result of which there is a clear view of the rotation shaft 7a as well as of the scales 9 and the discharge opening 10. By the same token, the encircling element 6a and the substrate 6d of the loading means are not shown in FIG. 8, so that the part of the pivot shaft 6c that protrudes towards the top above the floor 4 and the impact sensor 6e are completely visible.

INDUSTRIAL APPLICABILITY

The subject matter of the invention can be used, especially in the pharmaceutical industry, for checking and processing as well as handling pharmaceutical products such as tablets. The special usefulness lies in the fact that the device is capable of operating in a completely hygienic manner and does not affect at all the clean processing of the next product to be processed, particularly when a switch is made within the device to a different medication or different pills, since the device can be optimally cleaned prior to switching over to the next product to be processed.

LIST OF REFERENCE NUMERALS 1 protective hood
1a front of 1
1b gasket of 1
1c lower front surface of 1
2 housing
3 hinged door
4 test chamber floor
5 singling means
6 loading means
6a encircling element of 6
6b indentation of 6
6c swivel shaft of 6
6d substrate of 6
6e impact sensor of 6
7 star feeder
7a rotation shaft of 7
8 receiving cell
9 scales
10 discharge opening
11 rectangular pipe
12 filling opening
13 handle for opening the protective hood
14 electric motor
15 test chamber below the protective hood 1
16 receiving chamber of the housing 2
17 device
18 collecting container
19 front wall of the housing 2
20 antechamber
21 front plate
21a screws
22 interface
23 frame
24 closing mechanism
G handle
S1,S2 hinge
V locks

The invention claimed is:

1. A device (17) for the quality control of solid pharmaceutical products comprising at least one testing means (9) having at least one sensor—and/or a height measuring means and/or a force measuring means for measuring the rupture strength of the product—for checking and ascertaining one or more parameters of the individual pharmaceutical product as well as comprising a transporting means (5, 6, 7) for the products, characterized in that the device (17) has a housing (2) and a test chamber (15) that is arranged above said housing and that can be sealed so as to be splash-proof or water-tight and dust-tight vis-à-vis the environment, said chamber being formed by a floor (4) and by a protective hood (1) that can be placed onto and lifted off this floor, whereby the testing means (9) as well as the transporting means (5, 6, 7) are located in said chamber.

2. The device according to claim 1, characterized in that all of the lines and/or drive shafts (6c, 7a) leading into or out of the test chamber (15) are configured so as to be splash-proof or water-tight and dust-tight as they pass through the protective hood (1) or the floor (4).

3. The device according to claim 2, characterized in that the floor (4) has at least one passage, especially for passing lines or a drive shaft (6c, 7a) through, said passage being sealed by means of a gasket that is splash-proof or water-tight and dust-tight.

4. The device according to claim 1, characterized in that the protective hood (1) can be pressed onto the periphery of the floor (4) of the test chamber (15) and locked in place so as to be splash-proof or water-tight and dust-tight, whereby the protective hood (1) has an encircling gasket (1b) that is splash-proof or water-tight and dust-tight on its surface (1c) facing the floor (4) of the test chamber (15).

5. The device according to claim 4, characterized in that the gaskets are inflatable O-ring gaskets.

6. The device according to claim 1, characterized in that an interface (22) that is accessible from outside of the housing (2) is arranged on the housing (2), preferably on its front wall (19), whereby a plurality of electric lines leading into or out of the housing (2) open into said interface and the latter serves to establish an electric connection for the device (7) and/or to transmit electric signals and/or data between the device (7) and the outside world.

7. The device according to claim 6, characterized in that a hinged door (3) is arranged on the housing (2) in such a way as to form an antechamber (20) between the housing (2) and the hinged door (3).

8. The device according to claim 7, characterized in that the discharge opening (10) is a hole in the floor (4) of the test chamber (15), and the collecting container (18) is located in the antechamber (20).

9. The device according to claim 1, characterized in that the device (17) encompasses the following additional components:

a singling means (5) as part of the transporting means (5, 6, 7) arranged inside the test chamber (15), whereby the pharmaceutical products can be fed from the storage container to the singling means;

a conveying means (7) as another part of the transporting means (5, 6, 7) that is arranged above the test chamber floor (4) and that has at least one receiving cell (8) open towards the floor (4) into which one product from the singling means (5) can be introduced, whereby the product accommodated in the receiving cell (8) can be fed to the testing means (9);

a discharge opening (10) to which the product—after it has been tested by the testing means (9)—can be fed during the further course of transportation by the conveying means (7), whereby the product reaches the discharge opening (10) and then falls through it, as a result of which it is removed from the receiving cell (8);

as well as a collecting container (18) situated below the discharge opening (10) that serves to receive the tested products or parts thereof once they have fallen through the discharge opening (10).

10. The device according to claim 9, characterized in that the transporting means (7) is a star feeder (7) that is arranged parallel to the floor (4) and that can rotate around a vertical axis, the receiving cell (8) is situated in the vicinity of the outer circumference of the star feeder (7), and the testing means (9) as well as the discharge opening (10) are arranged in such a way that, as the star feeder (7) turns in its direction of rotation, each product accommodated inside the receiving cell (8) first reaches the testing means (9) and subsequently the discharge opening (10).

11. The device according to claim 9, characterized in that the test chamber floor (4) has a rim around the discharge opening (10).

12. The device according to claim 1, characterized in that the protective hood (1) can be connected in a detachable manner to the floor (4) of the test chamber (15) so as to be splash-proof or water-tight and dust-tight.

13. The device according to claim 1, characterized in that the housing (2) can likewise be sealed so as to be splash-proof or water-tight and dust-tight.

14. The device according to claim 1, characterized in that means for driving, controlling and supplying one or more testing means (9) and one or more transporting means (5, 6, 7) are arranged in the housing (2).

15. The device according to claim 1, characterized in that all inlet or feed openings (12) leading into the test chamber (15) as well as all outlet or discharge openings (12) leading out of the test chamber (15) can be hermetically sealed so as to ensure that the test chamber (15) is splash-proof or water-tight.

16. The device according to claim 1, characterized in that the floor (4) of the test chamber (15) is, at the same time, the wall of the housing (2).

17. The device according to claim 1, characterized in that means for driving, controlling and supplying the testing means (9) and the transporting means (5, 6, 7), such as drive aggregates, electric motors, electric controls, signal amplifiers as well as electric and/or optical and/or mechanical connections to supply energy to the testing means (9) are all arranged inside the housing (2).

18. The device according to claim 1, characterized in that the testing means (9) is a set of scales (9) equipped with a weighing platform and a load cell.

19. The device according to claim 1, characterized in that the inside of the housing (2) can be charged with positive pressure relative to the environment and/or to the test chamber (15).

20. The device according to claim 1, characterized in that the test chamber (15) can be charged with negative pressure relative to the environment.

21. The device according to claim 1, characterized in that the housing (2) is situated next to the floor of the test chamber (15) rather than below it.

22. The device according to claim 1, characterized in that the device has rollers or wheels on which the device (17) can be moved.

23. The device according to claim 1, characterized in that the front wall (19) of the housing (2) consists of a frame (22) and of a removable front plate (21) that can be placed onto the frame so as to be water-tight.

24. A device (17) for the quality control of solid pharmaceutical products selected from the group consisting of tablets, pills, oblongs and mixtures thereof, comprising at least one testing means (9) having at least one sensor scale (9) and/or a height measuring means and/or a force measuring means for measuring the rupture strength of the product—for checking and ascertaining one or more parameters of the individual pharmaceutical product as well as comprising a transporting means (5, 6, 7) for the products, characterized in that the device (17) has a housing (2) and a test chamber (15) that is arranged above said housing and that can be sealed so as to be splash-proof or water-tight and dust-tight vis-à-vis the environment, said chamber being formed by a floor (4) and by a protective hood (1) that can be placed onto and lifted off this floor, whereby the testing means (9) as well as the transporting means (5, 6, 7) are located in said chamber.

25. A device (17) for the quality control of solid pharmaceutical products comprising at least one testing means (9) having at least a member selected from the group consisting of one sensor, a height measuring means and a force measuring means for measuring the rupture strength of the product—for checking and ascertaining one or more parameters of the individual pharmaceutical product;

a transporting means (5, 6, 7) for the products;

a housing (2);

a floor (4);

a protective hood (1) that can be placed onto and lifted off this floor, wherein the floor (4) and the protective hood (1) form a test chamber (15) that is arranged above said housing and that can be sealed so as to be splash-proof or water-tight and dust-tight vis-à-vis the environment, wherein the testing means (9) as well as the transporting means (5, 6, 7) are located in said test chamber.

* * * * *